United States Patent
Edginton

(10) Patent No.: US 9,199,041 B2
(45) Date of Patent: Dec. 1, 2015

(54) SYRINGE CAP REMOVER

(75) Inventor: Alex Edginton, Oxfordshire (GB)

(73) Assignee: OWEN MUMFORD LIMITED, Oxford (GB)

(*) Notice: Subject to any disclaimer, the term of this patent is extended or adjusted under 35 U.S.C. 154(b) by 845 days.

(21) Appl. No.: 13/381,720

(22) PCT Filed: Jun. 21, 2010

(86) PCT No.: PCT/GB2010/051022
§ 371 (c)(1),
(2), (4) Date: Apr. 12, 2012

(87) PCT Pub. No.: WO2011/001161
PCT Pub. Date: Jan. 6, 2011

(65) Prior Publication Data
US 2012/0186075 A1    Jul. 26, 2012

(30) Foreign Application Priority Data

Jun. 30, 2009 (GB) .................................. 0911291.3

(51) Int. Cl.
*A61M 5/32* (2006.01)
*A61M 5/20* (2006.01)
*A61M 5/24* (2006.01)

(52) U.S. Cl.
CPC ........... *A61M 5/3204* (2013.01); *A61M 5/2033* (2013.01); *A61M 5/24* (2013.01); *A61M 5/3202* (2013.01); *A61M 2005/2407* (2013.01); *A61M 2005/2488* (2013.01); *Y10T 29/53* (2015.01)

(58) Field of Classification Search
CPC . A61M 5/3204; A61M 5/00; Y10T 29/53987
USPC ..................................... 29/255; 604/192, 198
See application file for complete search history.

(56) References Cited

U.S. PATENT DOCUMENTS

| 5,137,516 A | 8/1992 | Rand et al. |
| 6,258,068 B1 | 7/2001 | Kirchhofer et al. |

(Continued)

FOREIGN PATENT DOCUMENTS

| GB | 2438593 A | 12/2007 |
| WO | 9630065 A1 | 10/1996 |

(Continued)

OTHER PUBLICATIONS

International Search Report, dated Oct. 22, 2010 from corresponding PCT application.
United Kingdom Search Report, dated Oct. 27, 2009, from corresponding GB application.

*Primary Examiner* — Lee D Wilson
*Assistant Examiner* — Jamal Daniel
(74) *Attorney, Agent, or Firm* — Young & Thompson

(57) ABSTRACT

An apparatus for removing a sheath from a syringe. The sheath provides a sterile cover for a needle of the syringe. The apparatus includes a substantially cylindrical housing defining an opening for receiving a sheath attached to a syringe, and a driver mounted on the housing and being slideable along the housing between first and second axially displaced positions. The apparatus further includes a plurality of radially deflectable fingers mounted within the housing and being coupled to the driver for movement therewith. The fingers are configured such that movement of the driver from the first to the second position causes the fingers to slide over the sheath and engage with a formation on the sheath. Movement of the driver from the second position towards the first position causes the fingers to push the sheath off the syringe. Also provided is an injection device including the apparatus.

7 Claims, 11 Drawing Sheets

(56) References Cited

U.S. PATENT DOCUMENTS

| | | |
|---|---|---|
| 8,900,197 B2 * | 12/2014 | Crow .......................... 604/197 |
| 2004/0010234 A1 | 1/2004 | Hung et al. |
| 2006/0100588 A1 | 5/2006 | Brunnberg et al. |
| 2006/0270986 A1 | 11/2006 | Hommann et al. |
| 2009/0270672 A1 * | 10/2009 | Fago ................................ 600/5 |

FOREIGN PATENT DOCUMENTS

| | | |
|---|---|---|
| WO | 0024441 A1 | 5/2000 |
| WO | 2006009508 A1 | 1/2006 |
| WO | 2006063015 A2 | 6/2006 |
| WO | 2007047200 A1 | 4/2007 |
| WO | 2008086004 A1 | 7/2008 |

* cited by examiner

SYRINGE CAP REMOVER

TECHNICAL FIELD

The present invention relates to syringe sheath removers and to injection devices incorporating such removers.

BACKGROUND

Various types of injection devices are available for assisting with the injection of a medicament into a patient (human or animal), and which are configured to receive a standard, pre-filled glass or plastic syringe tipped with an injection needle. These devices may have a dose setting mechanism and a main drive spring for driving a plunger into the syringe so as to expel the medicament out through the needle. Injection devices may comprise a further spring for driving the needle out of the device housing and into the patient's skin, prior to activation of the main drive spring to expel the medicament.

In order to maintain sterility prior to use, and to avoid "sticking" injuries, the pre-filled syringe is supplied to the injection device assembler with a rubber or rubber and plastic cap, known as a "sheath" or "boot", covering the needle. The sheath has an interior space for containing the needle, and a sealing end that abuts the adjacent end of the syringe body to seal that inner space. In some cases, the sheath may also comprise a solid piece into which the needle is pushed. Immediately prior to use, a user (e.g. healthcare professional or patient) must remove the sheath to uncover the needle. This is typically achieved using a sheath removal tool that is inserted by a user into the injecting end of the device. The tool comprises a set of sprung fingers that ride over and along the sheath as the tool is pushed into the device. The fingers then snap into the junction between the syringe end and the sheath. The user can then pull out the tool, bringing the cap with it.

Particularly in the case of expensive medicaments, it is extremely important to minimise the failure rate of assembled injection devices. Considering the sheath removal solution outlined in the previous paragraphs, it may be difficult to achieve exactly the right degree of flexibility in the fingers to ensure that they can ride over the sheath whilst still providing sufficient force to close over the junction at the rear of the sheath.

GB 2438593 (Cilag), US2006/0100588 A1 (Brunnberg et al), WO 2007/047200 A1 (Eli Lilly), US 2006/0270986 A1 (Hommann et al), WO 2006/063015 A2 (Washington Biotech Corp.) and US 2004/010234 A1 all describe devices for housing syringes and removing sheaths therefrom.

SUMMARY

It is an object of the present invention to provide a sheath removal mechanism that is both easy to use and reliable, reducing the failure rate of assembled injection devices.

According to a first aspect of the present invention there is provided apparatus for removing a sheath from a syringe, the sheath providing a sterile cover for a needle of the syringe, the apparatus comprising:
- a substantially cylindrical housing defining an opening for receiving a sheath attached to a syringe;
- a driver mounted on the housing and being slideable along the housing between first and second axially displaced positions; and
- a plurality of radially deflectable fingers mounted within said housing and being coupled to said driver for movement therewith, the fingers being configured such that movement of said driver from said first to said second position causes said fingers to slide over said sheath and engage with a formation on said sheath, and movement of the driver from said second position towards said first position causes said fingers to push the sheath off the syringe.

By coupling the fingers to a driver slideable on the housing, embodiments of the invention are provided with a greater level of control. Indeed, this arrangement allows the sheath to be easily removed in a smooth manner, thus preventing it from being inadvertently dropped on the floor, for instance.

In an embodiment of the invention, the formation on the sheath is an end of the sheath adjacent to a shoulder of the syringe body. Alternatively, the formation on the sheath may be a notch on the body of the sheath arranged to cooperate with the fingers of the apparatus.

The driver may comprise one or more corrugations or protrusions. These enable the user to grip the driver more easily, especially if the user is wearing latex gloves, for instance.

The driver may be in the form of a sleeve arranged coaxially about the housing over which it slides. For example, the driver may be substantially cylindrical. The driver may be formed from one or more, for instance two, cooperating parts that are snapped together around the outside of the housing.

The housing may define one or more axially extending slots through which the driver is coupled to the fingers, for instance by one or more arms, with the arm(s) being slideable along the slot(s) as the driver is moved between said first and second positions.

The apparatus may comprise a collar within the housing, said fingers depending from the collar. The fingers may be formed integrally with the fingers. Said arms may be formed integrally with said collar or with said driver.

The apparatus may comprise a driver return spring located within said housing and configured to bias said driver towards said first position. The driver return spring may be coupled at one end to said collar and at its other end to the housing.

According to a second aspect of the present invention there is provided an injection device for assisting with the injection of medicament from a syringe, the device comprising apparatus according to the above first aspect of the invention. In some embodiments, the injection device further comprises a pre-filled syringe having a needle and a sheath providing a sterile cover for the needle.

Said housing may be a main housing of the injection device arranged to receive a syringe. The injection device may further comprise a syringe return spring tending to push the syringe into the housing and away from an injecting end, such that once the sheath is removed and the driver released, the syringe and its needle are pushed back into the housing. The syringe return spring may be couple at one end to the housing and at another end to the syringe.

DETAILED DESCRIPTION

Apparatus will now be described that enables the easy and reliable removal of a sheath or cap covering a needle of a pre-filled syringe. As has already been outlined above, an assembler of injection devices (e.g. auto-injectors and the like) will typically obtain pre-filled syringes from a supplier. The assembler may have little or no influence over the design of the syringes including the sheaths, and may therefore have to ensure that its device design and assembly process is compatible with the syringe design.

Figure 1:
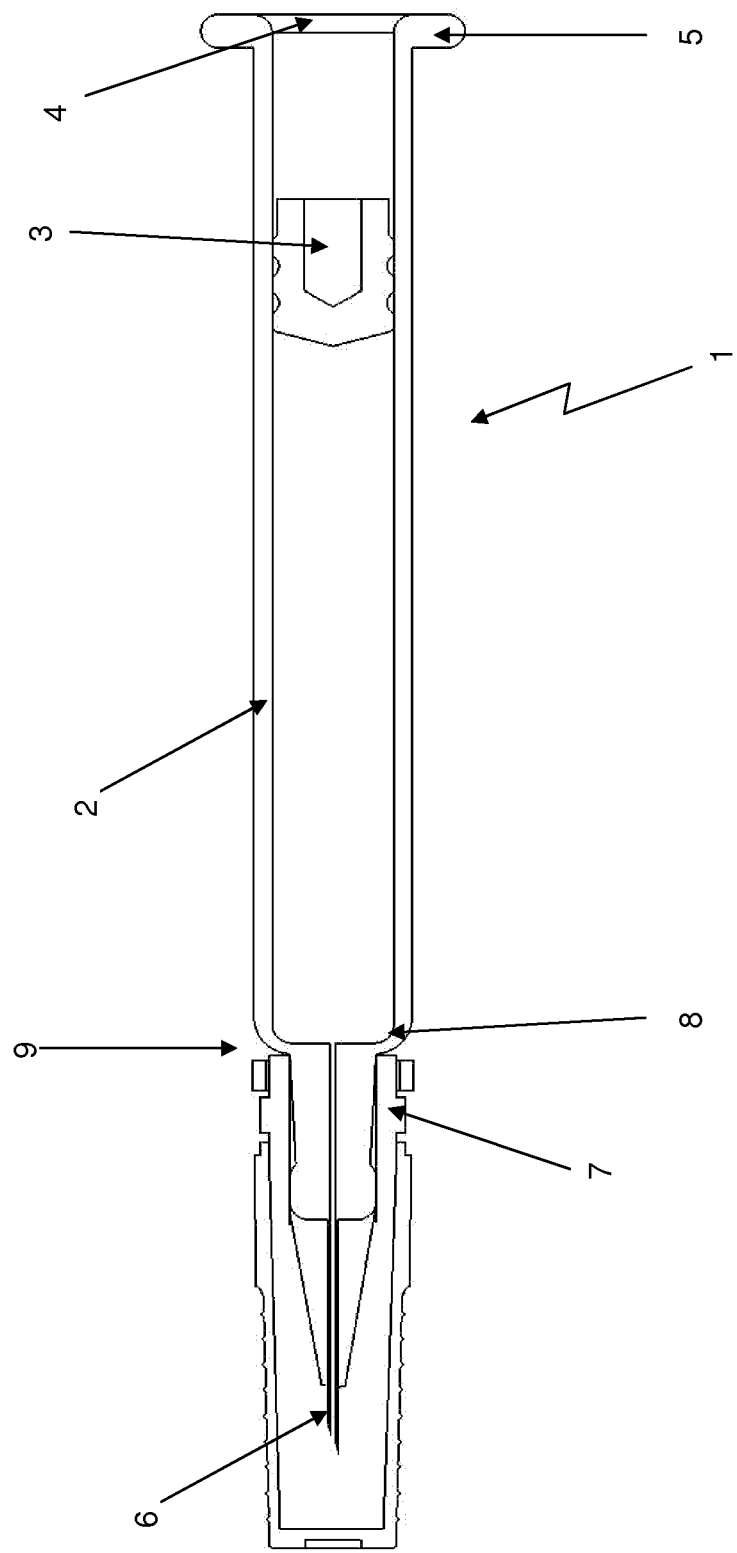
FIG. 1 illustrates a syringe with a sheath covering a syringe needle.

FIG. 1 shows a conventional syringe 1, comprising a body 2 containing the medicament, a plunger 3 located within the body and which may extend outwardly therefrom, an annular lip 4, wings 5 and a hypodermic needle 6 coupled to the opposite end of the body. An essentially solid rubber or rubber and plastics sheath 7 covers the needle 6 and seals around a shoulder portion of the syringe body 2. An additional sheath cover 33 is shown provided on the outside of the sheath 5. At the junction between the shoulder 8 of the sheath 7 and the distal end of the body 2, a small axial gap, channel or formation 9 exists.

Figure 2:
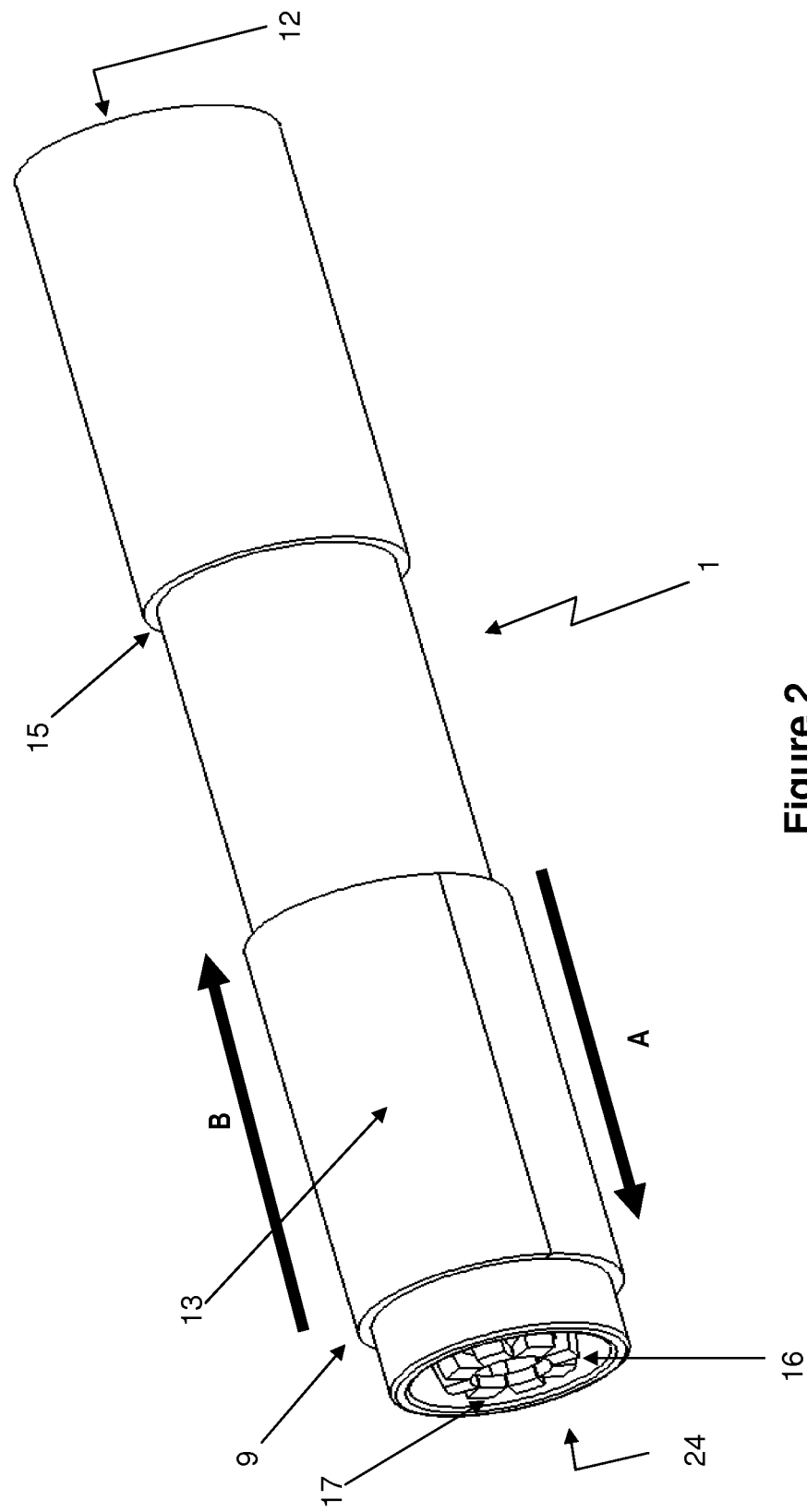
FIG. 2 illustrates a sheath remover for use with the syringe of FIG. 1.

FIG. 2 is a perspective view of an assembled sheath remover 10. The remover comprises a generally cylindrical casing or housing 11, defining an opening 12. The housing 11 is provided with locating formations for retaining an inserted syringe 1 and is of a rigid plastics material. The sheath remover 10 further comprises a driver sleeve 13 which is slideable on the housing 11 back and forth between a first position 14 and a second position 15, see arrows A and B in FIG. 2. The driver sleeve 13 cooperates with clamping fingers 16, having ends 17, such that the fingers also move in the direction of arrows A and B upon movement of the driver sleeve 13. The sheath remover is described in more detail below.

Figure 3:
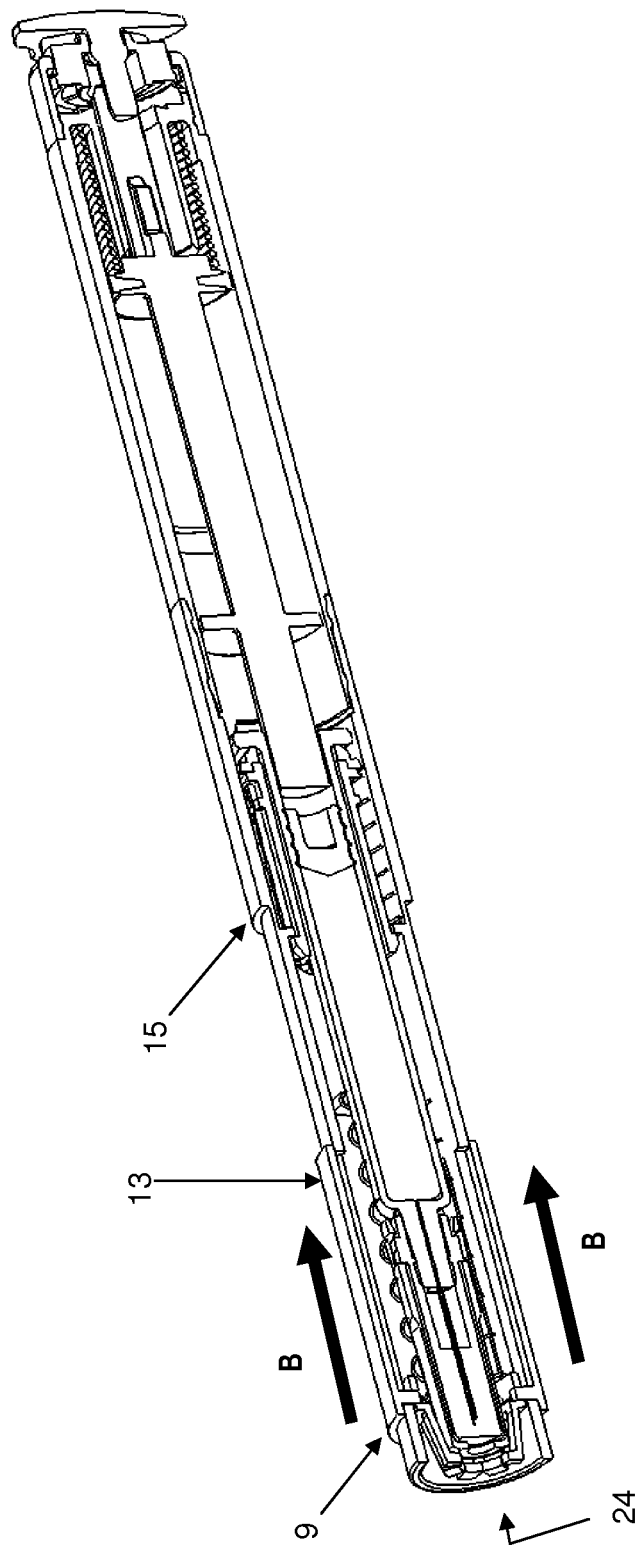
FIG. 3 illustrates an injection device comprising the sheath remover of FIG. 2 and loaded with the syringe of FIG. 1.

FIG. 3 shows an injection device 18. The injection device 18 comprises a casing 19 and a dose delivery mechanism 20 to inject the medicament (and insert the needle if this functionality is provided). The sheath remover of FIG. 2 is connected to an end of the injection device 18 by complimentary screw threads.

Figure 4:
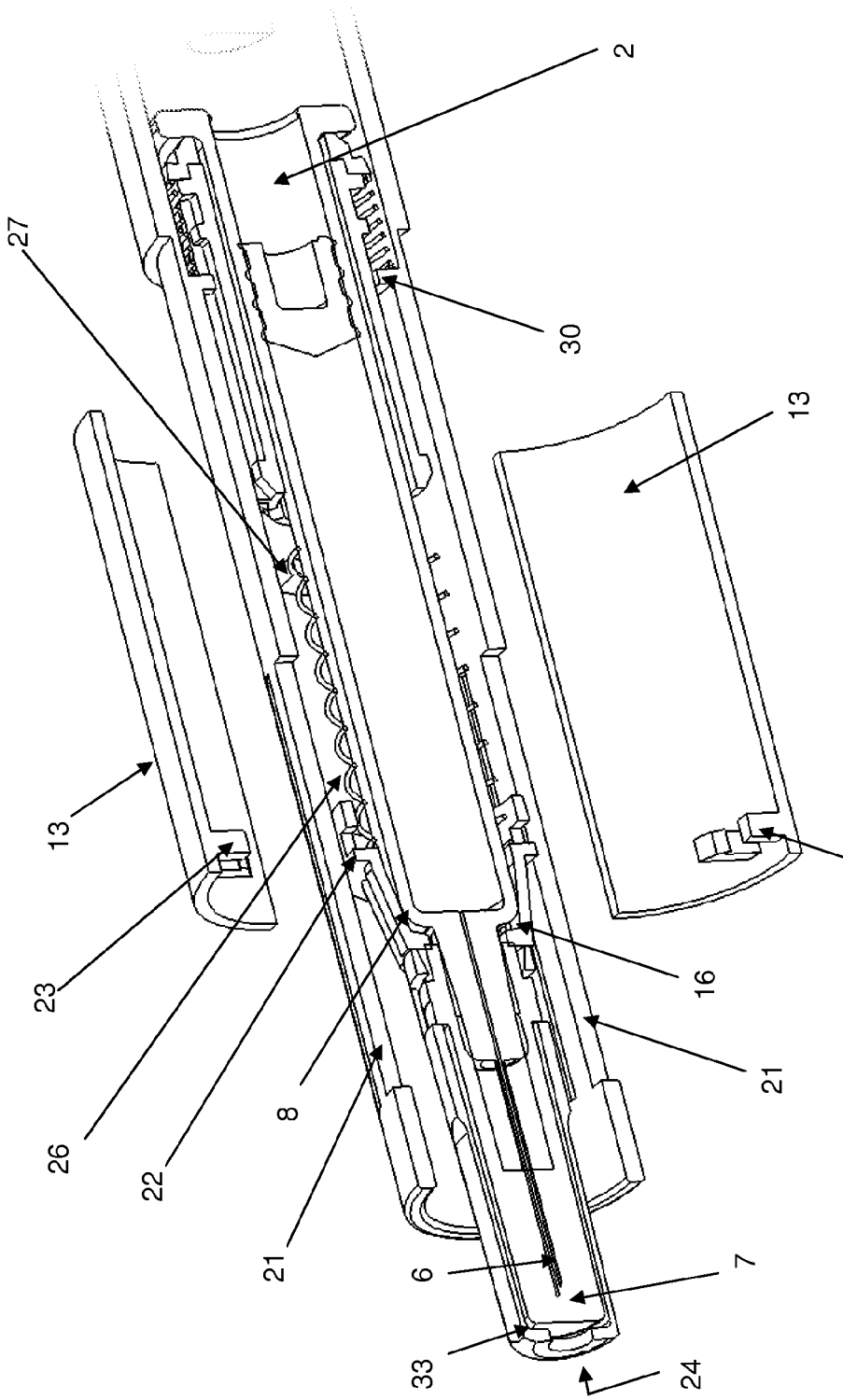
FIG. 4 illustrates a cross-section of the sheath remover of FIG. 2, partially exploded, and loaded with a syringe.

FIG. 4 shows the syringe and, in more detail, a cross-section through the sheath remover 10. The sheath remover comprises two components. A first of these components, the driver sleeve 13, comprises a partially cylindrical body (shown as two separate pieces in this exploded view) which engages, through a pair of slots 21 in the housing 11, with a collar 22 by means of a pair of respective depending arms 23. As the driver sleeve 13 is slideable on the housing 11, movement of the driver sleeve 13 leads to corresponding movement of the collar and the fingers, relative to the housing 11.

The fingers 16 are resilient and depend from an end of the collar 22 towards the injecting end 24 of the device, the injecting end 24 accommodating the sheath 7 of the syringe. It will be appreciated that in the absence of an additional restraining force, the clamping fingers 16 exhibit a small degree of flexibility in a radial direction.

The fingers 16 are arranged for snap-engagement with the gap 9 between the sheath 7 and the syringe body 2, as described further below. The fingers 16 are provided with ramps 25 on their inward facing sides for contacting the sheath 7. The fingers 16 are also provided with ends 17 to abut the sheath 7 when the fingers are engaged in the gap 9.

A driver return spring 26 acts at one end against the collar 22 and at its other end against a blocking member 27. The driver return spring 26 thus urges the collar 22 and driver sleeve 13 towards the injecting end 24 of the device, namely towards the first position 14 in the direction of arrow A as shown in FIG. 2.

Figure 5:
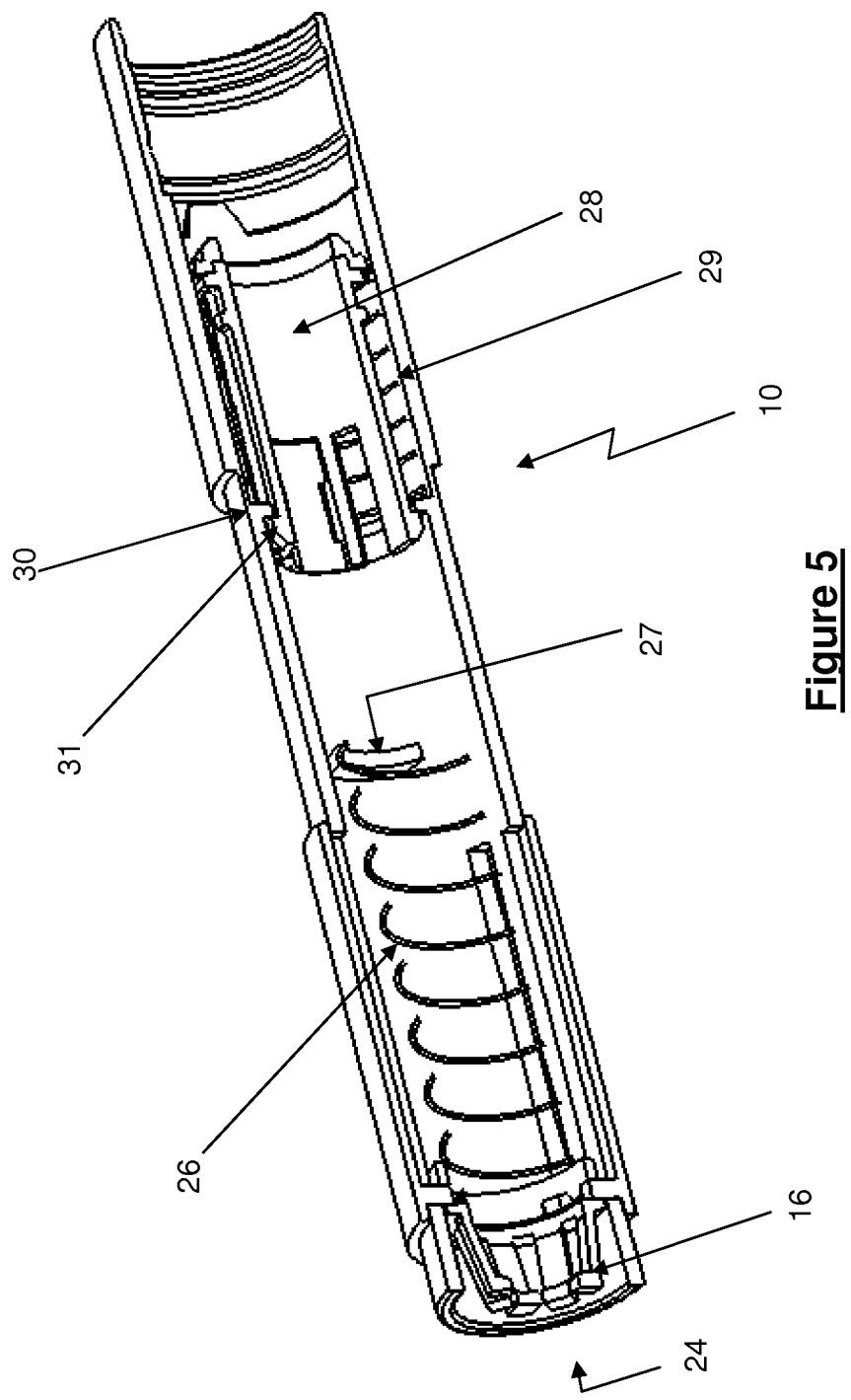
FIG. 5 illustrates, in a more detailed cross-section, the sheath remover of FIG. 2.

Referring to FIG. 5, the sheath remover 10 also comprises a syringe carrier 28 within the housing 11. A carrier return spring 29 is positioned between, and acts upon, annular end point 30 of the housing 11 and the carrier 28. The carrier return spring 29 thus urges the carrier 28 rearward (away from the injecting end 24).

Figure 7:
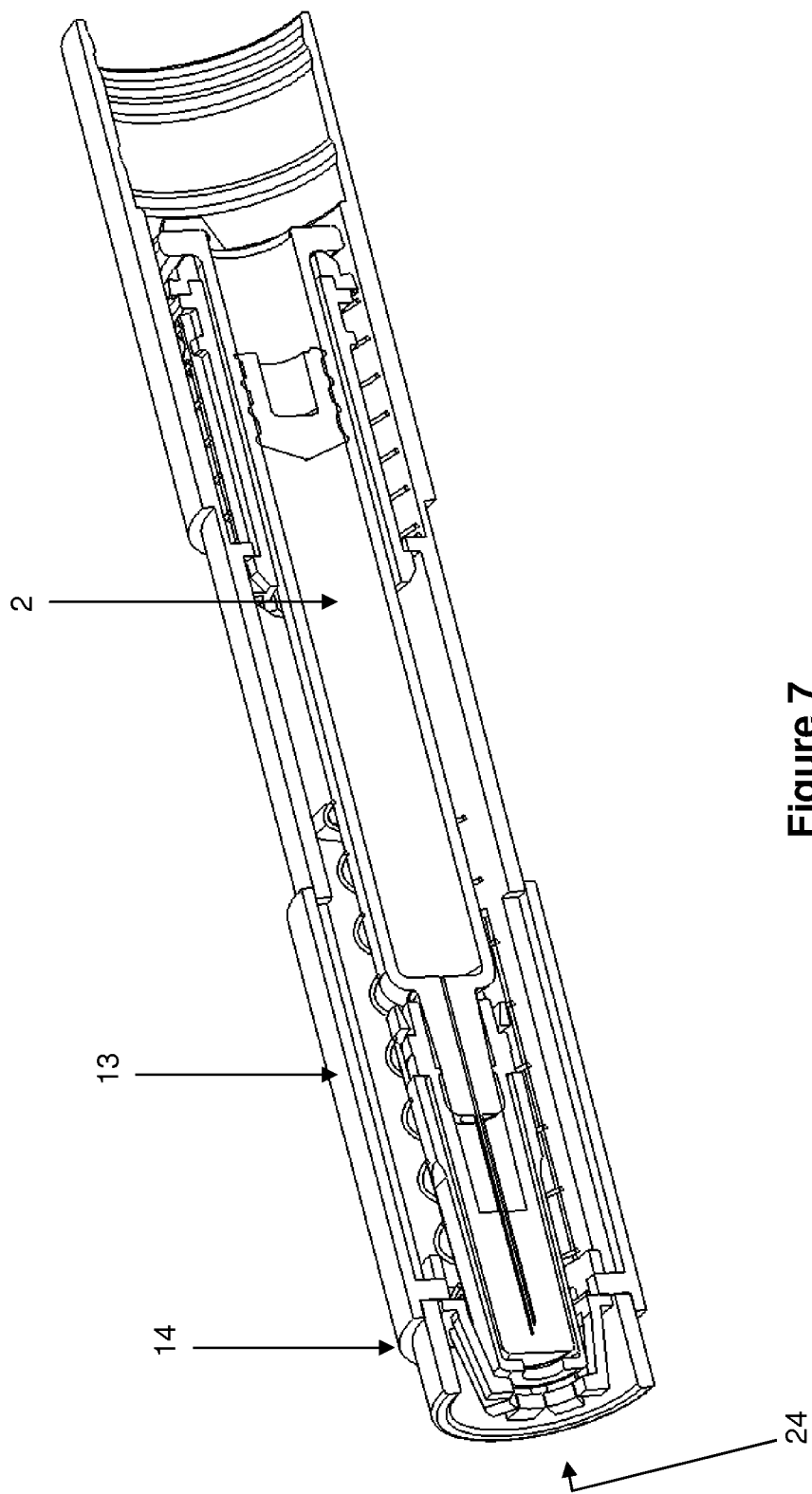
FIG. 7 illustrates in cross-section an assembled state of the sheath remover of FIG. 2.

The carrier 28 is adapted to contact and retain the wings 5, described earlier with reference to FIG. 1, provided at the end of the syringe body 4, once the syringe has been inserted into the device, as described below with reference to FIG. 7. The carrier 28 is itself slideable forwards (in the direction of injecting end 24) and rearwards (away from injecting end 24) within the housing. Forward and rearward protrusions 31 and 32 limit the extent of the movement of the carrier 28 by acting on the end point 30 on the housing 11. The rearward protrusion 32 stops the carrier 28 at limit of its forward movement by abutting end point 30. Similarly, forward protrusion 31 stops the carrier 28 at limit of its rearward movement by abutting end point 30.

In the absence of the syringe, as shown in FIG. 5, the carrier 28 is urged rearwards (away from injecting end 24), so that forward protrusion 31 abuts end point 30. At the same time, driver return spring 26 urges the collar 22, and therefore also the driver sleeve 13 and fingers 16, forwards (in the direction of injecting end 24). FIG. 5 shows that both driver return spring 26 and, in particular, carrier return spring 29 are fully extended in the absence of the syringe.

Figure 6:
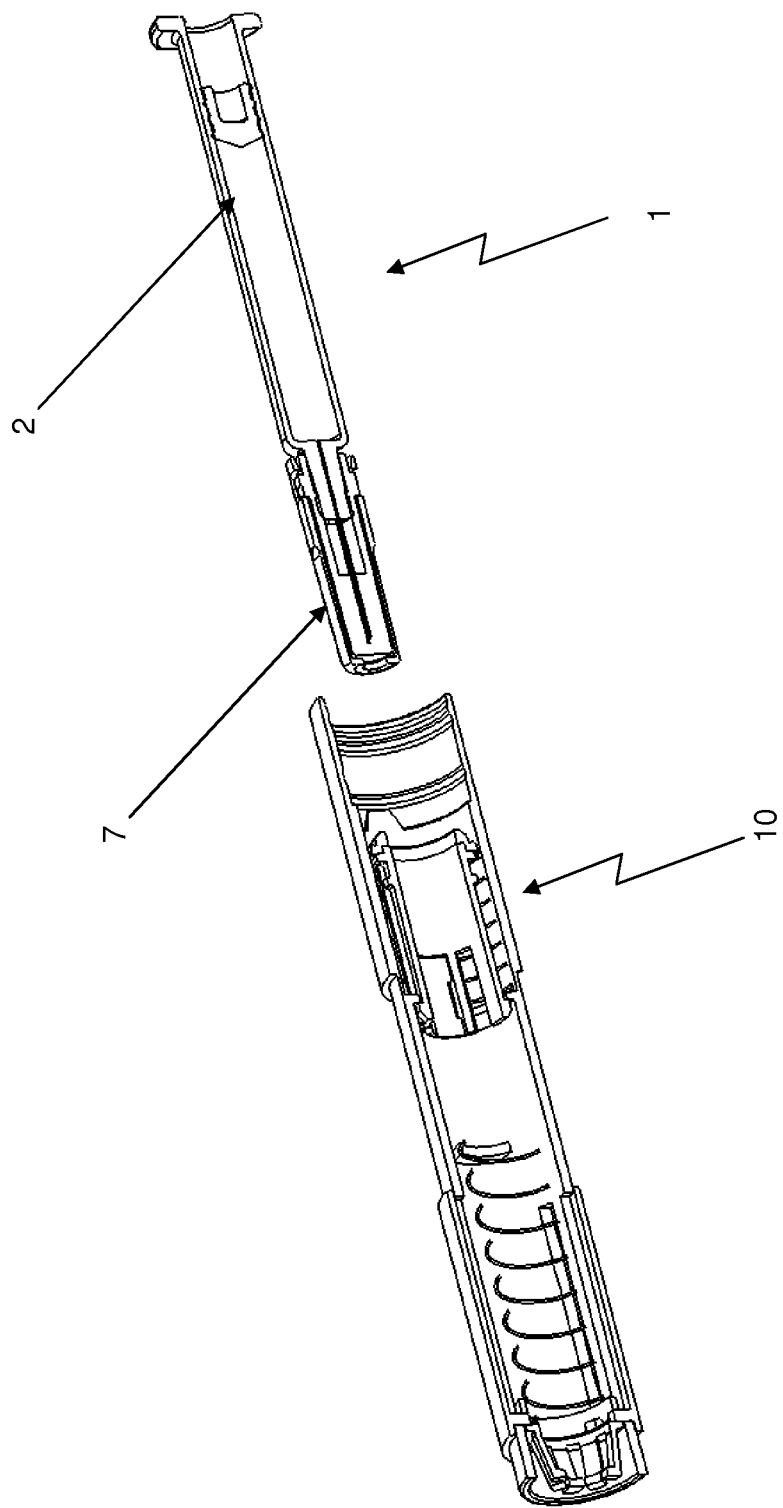
FIG. 6 illustrates in cross-section a first intermediate assembly state of the sheath remover and syringe of FIGS. 1 and 2.

The insertion of the syringe into the sheath remover will now be described. FIGS. 6 and 7 illustrate assembly stages of the syringe and sheath remover 10 of FIGS. 1 and 2. As the syringe 1 is pushed into the housing 11 of the sheath remover 10, the syringe body 2 passes through opening 12 until lip 4 and wings 5 engage with the carrier 28. In this position, the carrier return spring is substantially in its extended state.

The proportions of the slots 21 and second position 15, as well as fingers 16 and driver sleeve 13, are such that the depending arm 23 of the driver sleeve 13 does not reach the ends of the slots 21, distal from the injecting end 24, before the fingers 16 have engaged the gap 9, when the driver sleeve 13 is slid towards second position 15.

Upon insertion of the syringe into the housing 11, the sheath 7 will eventually come into contact with the ramps 25 formed on respective clamping fingers 16, as shown in FIG. 5. At this point, the driver sleeve 13 is in the first position 14, proximal to the injecting end 24, due to the action of the driver return spring 26. The driver return spring 26, like the carrier return spring, is substantially in its extended state.

Once the syringe 1 and sheath 7 have been inserted into the housing 11 of the sheath remover 10, other injection device components are inserted into the housing, behind the syringe, for instance by screwing the sheath remover 10 into casing 19, as described above. This aids in locking the syringe in place. This is shown in FIG. 7.

Use of the sheath remover to remove the sheath will be described with reference to FIGS. 8 to 11.

Figure 8:
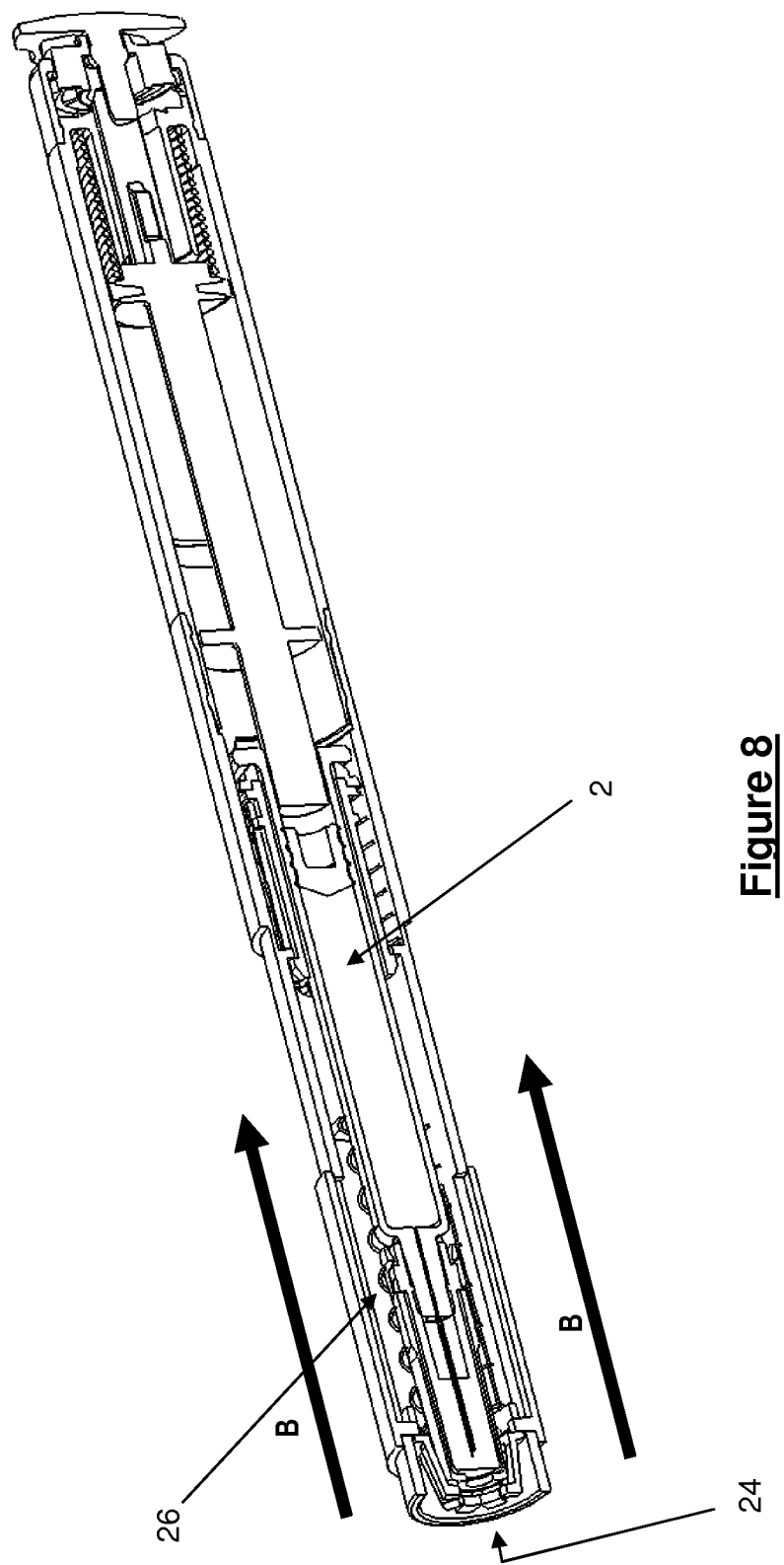
FIG. 8 illustrates in cross-section the sheath remover and syringe of FIG. 7 at a first intermediate stage of a sheath removal procedure.

To remove the sheath 7, the user grips driver sleeve 13 and moves it from the first position 14, along the housing 11, towards the second position 15, in the direction of arrow B in FIG. 8, thereby urging the ends 17 of the fingers 16 against the end of the sheath 7 distal to the syringe body 2.

Figure 9:
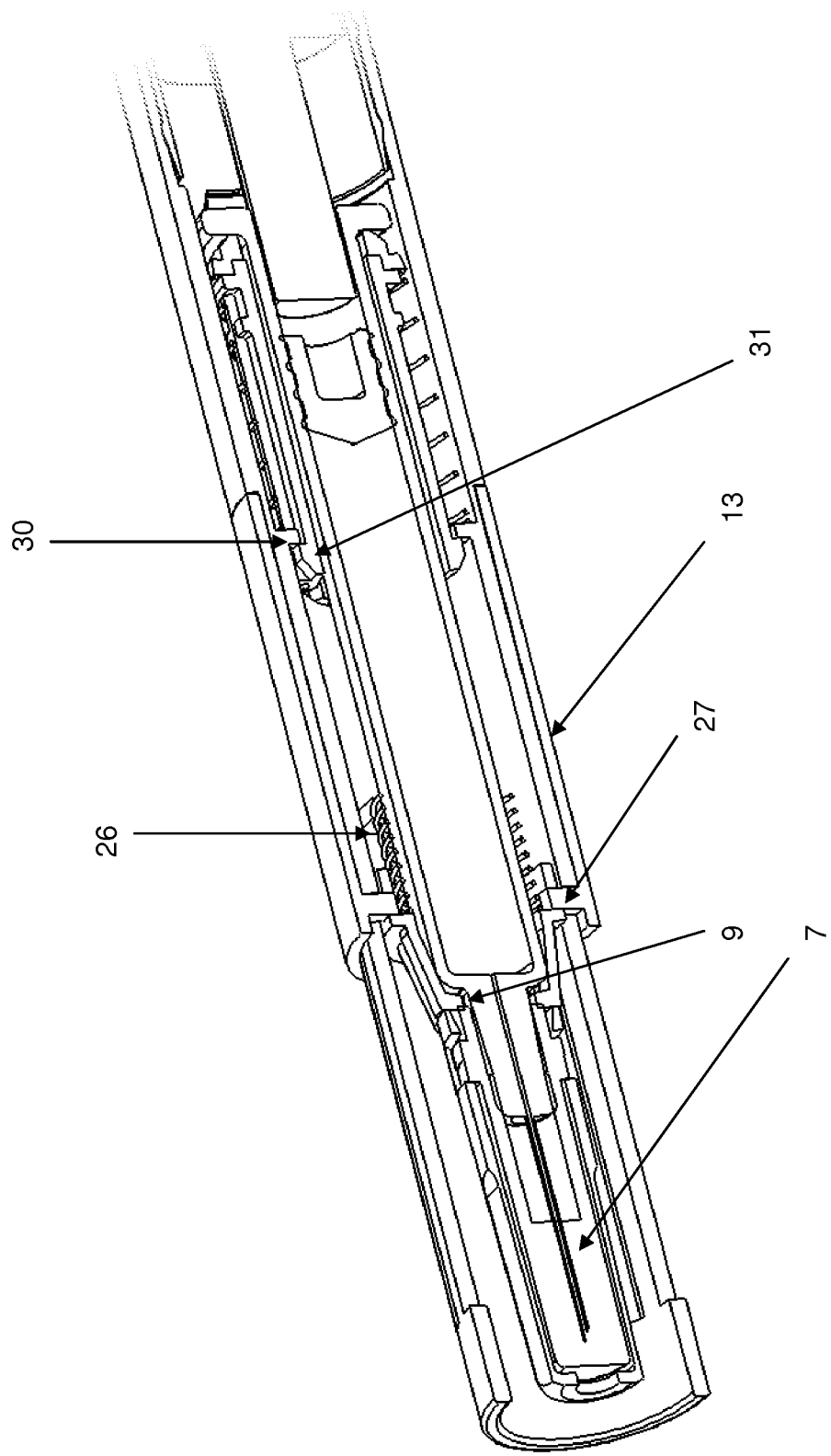
FIG. 9 illustrates in cross-section the sheath remover and syringe of FIG. 7 at a second intermediate stage of a sheath removal procedure.

Due to the presence of the ramps 25, the sheath 7 will deflect these fingers outward to a small extent, causing them to ride up and travel across the sheath as the driver sleeve 13 is moved towards second position 15—see FIGS. 8 and 9 which show intermediate stages of the sheath removal process.

Once the driver sleeve 13 has been moved to the second position 15 as shown in FIG. 9, the fingers 16 have been pulled the full length of the sheath 7, such that the clamping fingers snap into the gap 9 formed at the junction between the sheath 7 and the syringe body 2.

Figure 10:
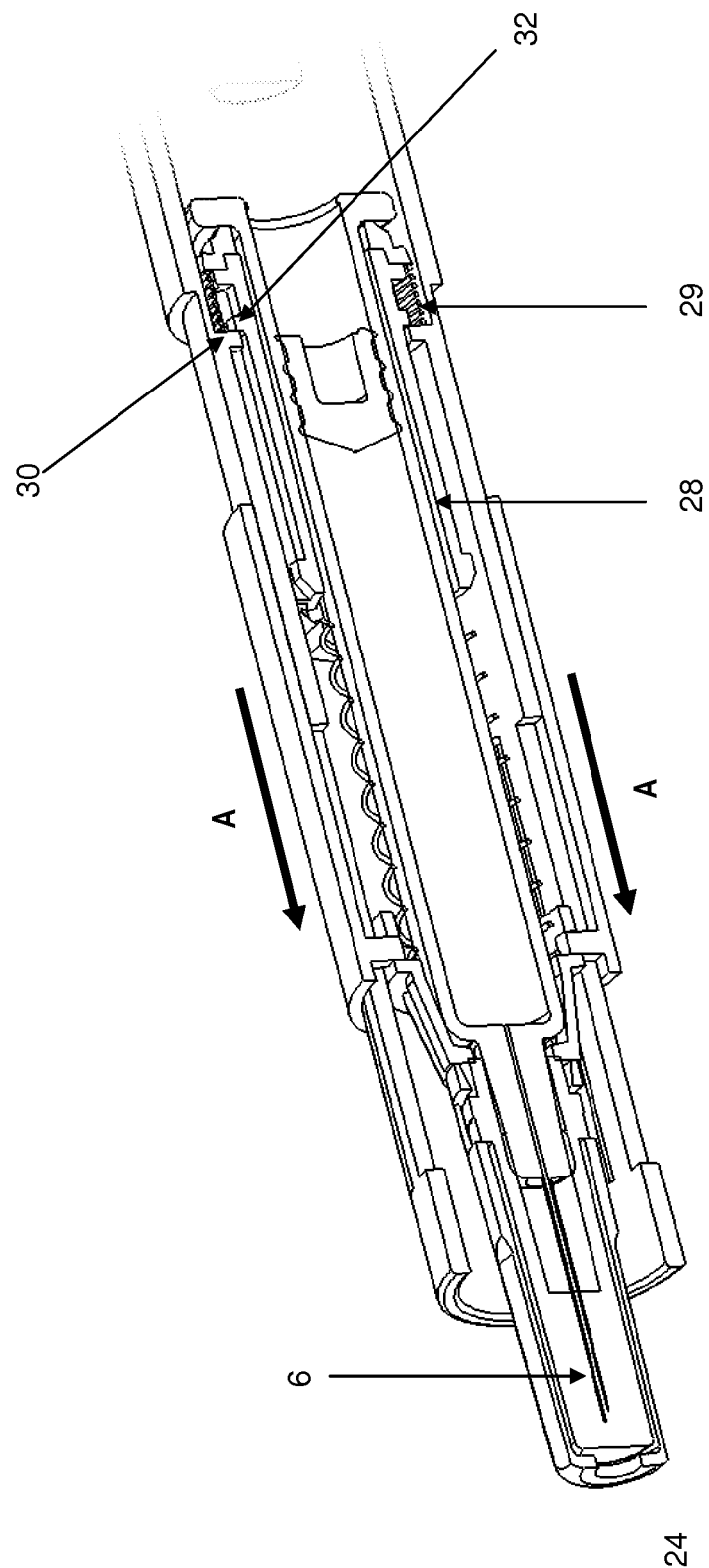
FIG. 10 illustrates in cross-section the sheath remover and syringe of FIG. 7 at a third intermediate stage of a sheath removal procedure.

The user then grasps the housing 11 and the driver sleeve 13, and pulls or pushes the latter back towards the injecting end 24, from the second position 15 towards the first position 14, as shown by arrow A in FIG. 10, representing the second stage of the sheath removal procedure. This causes the ends 17 of clamping fingers 16 to abut against the sheath 7 in the gap 9.

Upon movement of the driver sleeve 13 towards the first position 14, i.e. in the reverse direction, the syringe body 2 is retained within the housing 11 of the remover on the carrier 28, by virtue of the lip 4 and the wings 5 on the syringe body 2. However, the carrier 28 itself slides forwards (in the direction of arrow A in FIG. 10). The carrier return spring 29 is thereby compressed between the carrier 28 and end point 30, until further forward movement of the carrier is prevented by the contact of the rearward protrusion 32 against the end point 30, as shown in FIG. 10. This contact prevents further forward motion of the carrier and, therefore, the syringe body.

Figure 11:
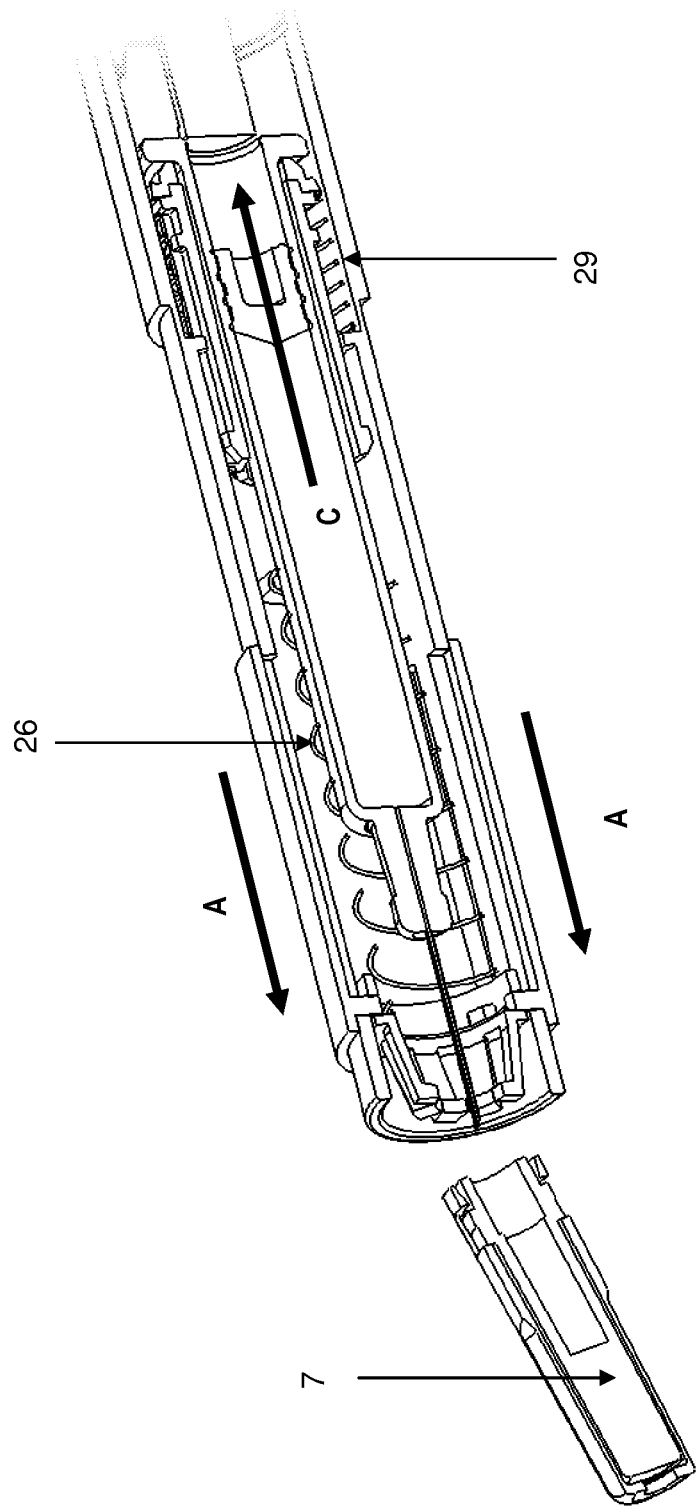
FIG. 11 illustrates in cross-section the remover and syringe of FIG. 7, with the sheath removed.

At this point, further forward movement of the driver sleeve 13 in the direction of arrow A in FIGS. 10 and 11 (and towards the first position 14), will continue to force the ends 17 of the fingers 16 against sheath 7, thereby urging the sheath off the needle 6. In the embodiment shown, the tip of the needle 6 protrudes beyond the injection end 24 of the sheath remover 10.

FIG. 11, being the third stage of the sheath removal process, shows how, by virtue of the restraint of the syringe body 2 and the abutment of the ends 17 of fingers 16 against the end of the sheath, further movement of the driver sleeve 13 in the direction of arrow A removes the sheath 7 from the needle 6.

Once the sheath 7 has been removed, the fingers no longer exert a pull on the syringe and the carrier return spring 29 urges the carrier 28 rearwards away from the injecting end 24, in the direction of arrow C in FIG. 11. In the embodiment shown, the exposed tip of the needle 6 is now retracted in the direction of arrow C. Thus, the tip of the needle 6 moves from an exposed position, beyond the injecting end 24, back within the housing 11.

It will be appreciated that, in some embodiments, the syringe carrier 28 is not required.

It will be appreciated by the person of skill in the art that various modifications may be made to the above described embodiments without departing from the scope of the invention. For example, rather than being configured for attachment to an end of an injection device, the sheath remover may be a separate component that is either used directly with a sheathed syringe, or is adapted to be inserted into an end of an injection device and removed once the sheath has been removed.

The invention claimed is:

1. An apparatus for removing a sheath from a syringe, the sheath providing a sterile cover for a needle of the syringe, the apparatus comprising:
    a substantially cylindrical housing defining an opening for receiving a sheath attached to a syringe;
    a driver mounted on the housing and being slideable along the housing between first and second axially displaced positions; and
    a plurality of radially deflectable fingers mounted within said housing and being coupled to said driver for movement therewith, the fingers being configured such that movement of said driver from said first to said second position causes said fingers to slide over said sheath and engage with a formation on said sheath, and movement of the driver from said second position towards said first position causes said fingers to push the sheath off the syringe,
    wherein the driver is in the form of a sleeve, said sleeve arranged coaxially about the housing and in slidable engagement therewith, and
    wherein the sleeve remains mounted on the housing in both said first and second positions.

2. The apparatus of claim 1, wherein the driver comprises one or more corrugations or protrusions.

3. The apparatus of claim 1, wherein the housing defines one or more axially extending slots through which the driver is coupled to the fingers.

4. The apparatus of claim 1, further comprising:
    a collar located within the housing, said fingers depending from the collar and said driver being coupled to said collar,
    wherein in use the syringe sheath passes through the collar.

5. The apparatus of claim 1, further comprising:
    a driver return spring located within said housing and configured to bias said driver towards said first position.

6. An injection device for assisting with the injection of medicament from a syringe, the device comprising:
    an apparatus for removing a sheath for providing a sterile cover for a needle of a syringe,
    wherein said apparatus comprises:
        a substantially cylindrical housing defining an opening for receiving a sheath attached to a syringe;
        a driver mounted on the housing and being slideable along the housing between first and second axially displaced positions; and
        a plurality of radially deflectable fingers mounted within said housing and being coupled to said driver for movement therewith, the fingers being configured such that movement of said driver from said first to said second position causes said fingers to slide over said sheath and engage with a formation on said sheath, and movement of the driver from said second position towards said first position causes said fingers to push the sheath off the syringe,
        wherein the driver is in the form of a sleeve, said sleeve arranged coaxially about the housing and in slidable engagement therewith, and
        wherein the sleeve remains mounted on the housing in both said first and second positions.

7. The injection device of claim 6, further comprising:
a syringe return spring tending to urge a syringe into the housing and away from an injecting end, such that once the sheath is removed and the driver released, the syringe and a needle of the syringe are pushed back into the housing.

\* \* \* \* \*